(12) United States Patent
Chan et al.

(10) Patent No.: US 9,199,992 B2
(45) Date of Patent: Dec. 1, 2015

(54) PROCESSES FOR THE PREPARATION OF AN APOPTOSIS-INDUCING AGENT

(71) Applicant: AbbVie Inc., North Chicago, IL (US)

(72) Inventors: Vincent S. Chan, Evanston, IL (US); Alan C. Christesen, Round Lake, IL (US); Timothy A. Grieme, Chicago, IL (US); Yi-Yin Ku, Buffalo Grove, IL (US); Mathew M. Mulhern, Lake Villa, IL (US); Yu-Ming M. Pu, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/644,970

(22) Filed: Mar. 11, 2015

(65) Prior Publication Data

US 2015/0183783 A1    Jul. 2, 2015

Related U.S. Application Data

(62) Division of application No. 14/207,179, filed on Mar. 12, 2014, now Pat. No. 9,006,438.

(60) Provisional application No. 61/780,621, filed on Mar. 13, 2013.

(51) Int. Cl.
*C07D 471/04* (2006.01)
*C07C 67/10* (2006.01)
*C07C 67/00* (2006.01)
*C07C 69/78* (2006.01)

(52) U.S. Cl.
CPC .............. *C07D 471/04* (2013.01); *C07C 67/00* (2013.01); *C07C 67/10* (2013.01); *C07C 69/78* (2013.01)

(58) Field of Classification Search
USPC ............................ 544/362; 546/113; 560/103
See application file for complete search history.

(56) References Cited

U.S. PATENT DOCUMENTS

| 8,084,607 B2 | 12/2011 | Bruncko et al. |
| 8,546,399 B2 | 10/2013 | Bruncko et al. |
| 8,580,794 B2 | 11/2013 | Doherty et al. |
| 8,722,657 B2 * | 5/2014 | Catron et al. ............ 514/210.01 |
| 2010/0022773 A1 | 1/2010 | Bruncko et al. |
| 2010/0305122 A1 | 12/2010 | Bruncko et al. |
| 2011/0124628 A1 | 5/2011 | Doherty et al. |
| 2012/0108590 A1 | 5/2012 | Birtalan et al. |
| 2012/0157470 A1 | 6/2012 | Catron et al. |
| 2012/0190688 A1 | 7/2012 | Bruncko et al. |
| 2012/0277210 A1 | 11/2012 | Catron et al. |
| 2013/0267514 A1 | 10/2013 | Brunko et al. |
| 2013/0267534 A1 | 10/2013 | Brunko et al. |
| 2014/0094471 A1 | 4/2014 | Brunko et al. |
| 2014/0113910 A1 | 4/2014 | Brunko et al. |

FOREIGN PATENT DOCUMENTS

| WO | 2011150016 A1 | 1/2011 |
| WO | 2012071336 A1 | 5/2012 |

OTHER PUBLICATIONS

Arredondo J.D., et al., "Preparation of t-Butyl-3-Bromo-5-Formylbenzoate Through Selective Metal-Halogen Exchange Reactions," Organic Syntheses, 2012, vol. 89, pp. 460-470.
Gassman P.G., et al., "A General Procedure for the Base-Promoted Hydrolysis of Hindered Esters at Ambient Temperatures," The Journal of Organic Chemistry, 1977, vol. 42 (5), pp. 918-920.
Rausis T., et al., "The Basicity Gradient-Driven Migration of Iodine: Conferring Regioflexibility on the Substitution of Fluorarenes," European Journal of Organic Chemistry, 2002, pp. 3351-3358.
Souers, Andrew J. et al, "ABT-199, a potent and selective BCL-2 inhibitor, achieves antitumor activity while sparing platelets," Nature Medicine, (2013), 9 pgs.
International Search Authority, "International Search Report for International Application No. PCT/US2014/024224," mailing date Jul. 30, 2014, 7 pages.
International Search Authority, "Written Opinion for International Application No. PCT/US2014/024224," mailing date Jul. 30, 2014, 9 pages.

* cited by examiner

*Primary Examiner* — Kristin Vajda

(57) ABSTRACT

Provided herein is a process for the preparation of an apoptosis-inducing agent, and chemical intermediates thereof. Also provided herein are novel chemical intermediates related to the process provided herein.

9 Claims, No Drawings

PROCESSES FOR THE PREPARATION OF AN APOPTOSIS-INDUCING AGENT

CROSS REFERENCE TO RELATED APPLICATION(S)

This application is a divisional application of U.S. application Ser. No. 14/207,179, which was filed Mar. 12, 2014, the disclosure of which is incorporated herein as if set forth in its entirety. U.S. application Ser. No. 14/207,179 claims priority from U.S. Provisional Application Ser. No. 61/780,621 filed Mar. 13, 2013, the disclosure of which is incorporated herein as if set forth in its entirety.

FIELD

Provided herein are processes for the preparation of an apoptosis-inducing agent, and chemical intermediates thereof. Also provided herein are novel chemical intermediates related to the processes provided herein.

BACKGROUND 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (hereafter, "Compound 1") is a potent and selective Bcl-2 inhibitor having, inter alia, antitumor activity as an apoptosis-inducing agent. Compound 1 has the formula:

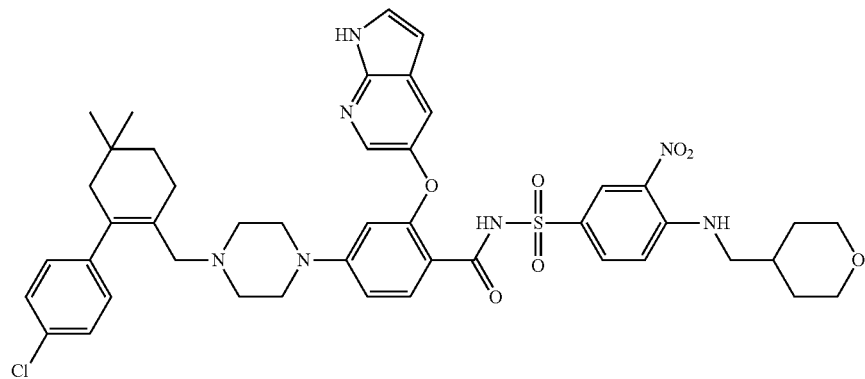

Compound 1 is currently the subject of ongoing clinical trials for the treatment of chronic lymphocytic leukemia. U.S. Patent Publication No. 2010/0305122 describes Compound 1, and other compounds which exhibit potent binding to a Bcl-2 family protein, and pharmaceutically acceptable salts thereof. U.S. Patent Publication Nos. 2012/0108590 and 2012/0277210 describe pharmaceutical compositions comprising such compounds, and methods for the treatment of neoplastic, immune or autoimmune diseases comprising these compounds. U.S. Patent Publication No. 2012/0157470 describes pharmaceutically acceptable salts and crystalline forms of Compound 1. The disclosures of U.S. 2010/0305122; 2012/0108590; 2012/0157470 and 2012/0277210 are hereby incorporated by reference herein in their entireties.

SUMMARY

Provided herein are processes for the preparation of Compound 1 of the formula:

(1)

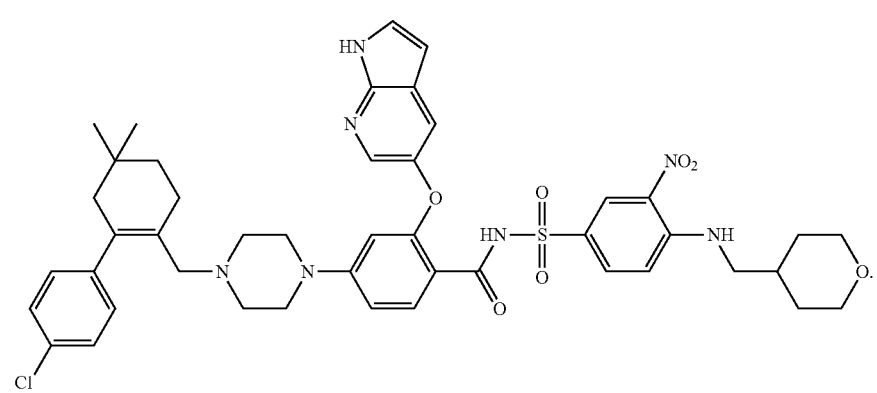

Also provided herein are compounds of the formulae:

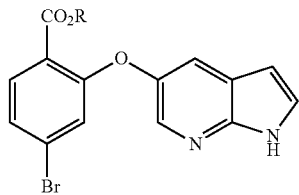

and

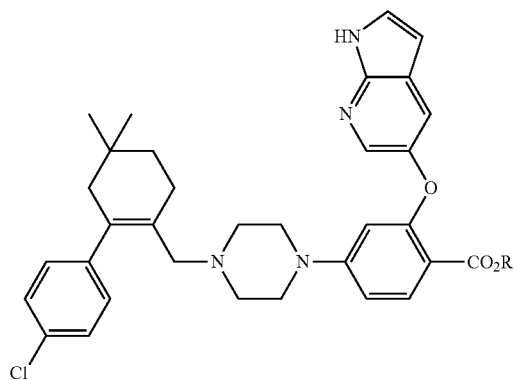

wherein R is $C_1$ to $C_{12}$ alkyl; and processes for their preparation.

DETAILED DESCRIPTION

Provided herein is a process for the preparation of Compound 1 of the formula:

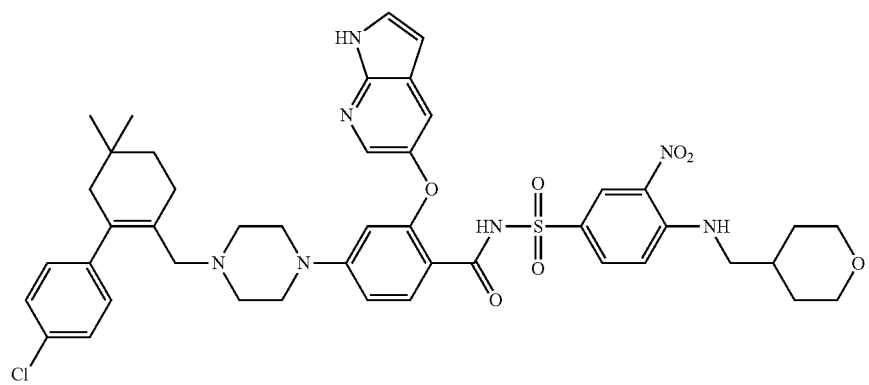

which comprises:

(a) combining a compound of formula (K):

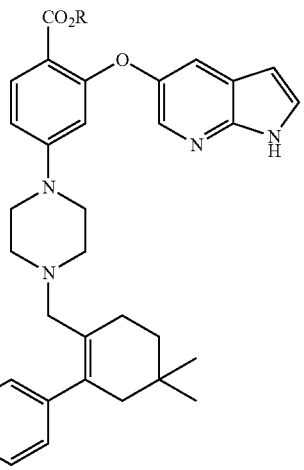

(K)

wherein R is $C_1$ to $C_{12}$ alkyl,
with a tert-butoxide salt, an aprotic organic solvent, and water to provide a compound of formula (L):

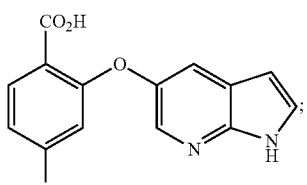

(L)

(b) combining the compound of formula (L) with a compound of formula (N):

(1)

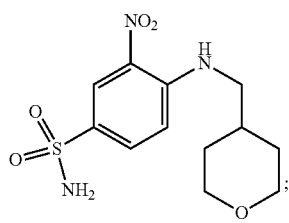

(N)

1-ethyl-3-(3-dimethylaminopropyl)carbodiimide hydrochloride (EDAC), 4-dimethylaminopyridine (DMAP), and an organic solvent to provide the compound of formula (1).

In some embodiments, R is $C_1$ to $C_6$ alkyl. In some embodiments, R is $C_1$ to $C_4$ alkyl. In some embodiments, R is selected from the group consisting of methyl, ethyl, n-propyl, isopropyl, n-butyl, tert-butyl, iso-butyl and neo-butyl. In some embodiments, R is tert-butyl.

In one embodiment, the process provided herein further comprises:

(c) combining a compound of formula (M):

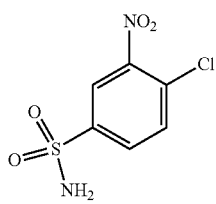

(M)

with (tetrahydro-2H-pyran-4-yl)methanamine, a tertiary amine base, and an organic solvent to provide the compound of formula (N).

In another embodiment, the process provided herein further comprises:

(d) combining a compound of formula (D):

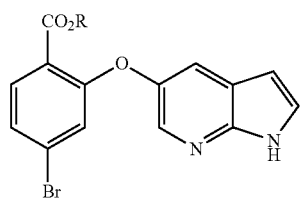

(D)

wherein R is $C_1$ to $C_{12}$ alkyl, with a compound of formula (I):

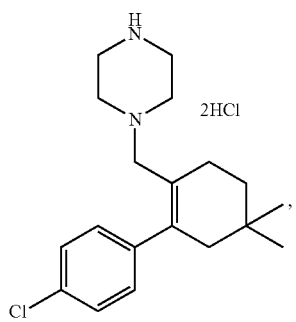

(I)

a source of palladium, a tert-butoxide salt, and a phosphine ligand in an aprotic organic solvent to provide the compound of formula (K).

In some embodiments, the phosphine ligand is a compound of formula (J):

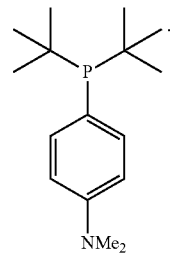

(J)

In another embodiment, the process provided herein further comprises:

(e) combining a compound of formula (B) with a compound of formula (C):

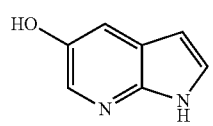

(B)

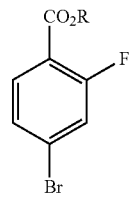

(C)

wherein R is $C_1$ to $C_{12}$ alkyl, and a tert-butoxide salt in an organic solvent to provide the compound of formula (D).

In another embodiment, the process provided herein further comprises:

(f) combining a compound of formula (A):

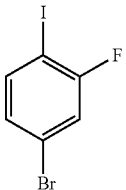
(A)

with R¹MgX in an aprotic organic solvent;

wherein R¹ is $C_1$ to $C_6$ alkyl; and X is Cl, Br or I;

(g) combining a $C_1$ to $C_{12}$ alkyl chloroformate or a di-($C_1$ to $C_{12}$ alkyl)dicarbonate with the product of step (f), to provide the compound of formula (C).

In another embodiment, the process provided herein further comprises:

(h) combining a compound of formula (E):

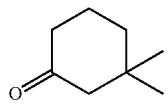
(E)

with DMF and $POCl_3$ to provide a compound of formula (F):

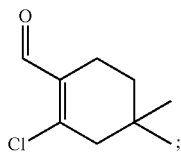
(F)

(i) combining the compound of formula (F) with a source of palladium and 4-chlorophenylboronic acid in an organic solvent to provide a compound of formula (G):

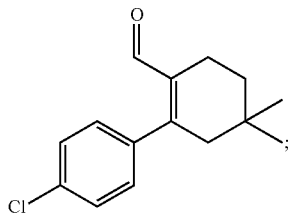
(G)

(j) combining the compound of formula (G) with BOC-piperazine and sodium triacetoxyborohydride in an organic solvent to provide a compound of formula (H):

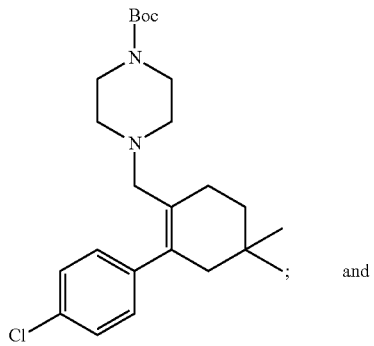
(H)

and (k) combining the compound of formula (H) with hydrochloric acid to provide the compound of formula (I).

In one embodiment, the process comprises steps (a) through (d). In one embodiment, the process comprises steps (a) through (e). In another embodiment, the process comprises steps (a) through (g). In another embodiment, the process comprises steps (a) through (k).

In one embodiment, the process comprises steps (a), (b) and (d). In another embodiment, the process comprises steps (a), (b), (d) and (e). In another embodiment, the process comprises steps (a), (b), (d), (h), (i), (j) and (k). In another embodiment, the process comprises steps (a), (b), (c), (d), (h), (i), (j) and (k). In another embodiment, the process comprises steps (a), (b), (d), (f), (g), (h), (i), (j) and (k). In another embodiment, the process comprises steps (a), (b), (d), (e), (f), (g), (h), (i), (j) and (k).

In some embodiments, in step (a) the tert-butoxide salt is selected from the group consisting of sodium tert-butoxide and potassium tert-butoxide. In some embodiments, in step (a) the tert-butoxide salt is sodium tert-butoxide. In some embodiments, in step (a) the tert-butoxide salt is potassium tert-butoxide.

In some embodiments, in step (a) the aprotic organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (a) the aprotic organic solvent is 2-methyltetrahydrofuran.

In some embodiments, in step (b) the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, in step (b) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (b) the organic solvent is dichloromethane.

In some embodiments, in step (c) the tertiary amine base is N,N-diisopropylethylamine.

In some embodiments, in step (c) the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, in step (c) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (c) the organic solvent is acetonitrile.

In some embodiments, in step (d) the compound of formula (I) is first combined with a base prior to the combining of step (d). In some embodiments, the base is an inorganic base. In some embodiments, the base is an organic base. In some embodiments, the base is selected from the group consisting of $K_3PO_4$, $Na_3PO_4$, NaOH, KOH, $K_2CO_3$ or $Na_2CO_3$. In some embodiments, the base is $K_3PO_4$. In some embodiments, in step (d) the compound of formula (I) is first combined with a base in one or more solvents prior to the combining of step (d).

In some embodiments, in step (d) the source of palladium is $Pd_2dba_3$ or $[(cinnamyl)PdCl]_2$. In some embodiments, in step (d) the source of palladium is $Pd_2dba_3$.

In some embodiments, in step (d) the tert-butoxide salt is selected from the group consisting of sodium tert-butoxide and potassium tert-butoxide.

In some embodiments, in step (d) the tert-butoxide salt is anhydrous. In some embodiments, in step (d) the tert-butoxide salt is anhydrous sodium tert-butoxide.

In some embodiments, in step (d) the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, in step (d) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (d) the aprotic organic solvent is a mixture of THF and toluene.

In some embodiments, step (d) further comprises the following steps:
(1) combining the tert-butoxide salt with the compound of formula (I) in an aprotic organic solvent;
(2) combining the source of palladium, the compound of formula (J), and the compound of formula (D) in an aprotic organic solvent; and
(3) adding the mixture of step (1) to the mixture of step (2).

In some embodiments, in step (d) the mixture resulting from step (2) is filtered prior to step (3).

In some embodiments, step (d) is carried out under an atmosphere of nitrogen or argon.

In some embodiments, in step (d) a catalytic amount of the source of palladium is used relative to the amount of compound (I). In some embodiments, the source of palladium is $Pd_2dba_3$ and the catalytic amount of $Pd_2dba_3$ is from about 0.5 mole percent to about 2 mole percent. In one embodiment, the catalytic amount of $Pd_2dba_3$ is about 0.75 mole percent.

In some embodiments, in step (d) a catalytic amount of the compound of formula (J) is used relative to the amount of compound (I). In some embodiments, the catalytic amount of the compound of formula (J) is from about 1 mole percent to about 5 mole percent. In one embodiment, the catalytic amount of the compound of formula (J) is from about 1 mole percent to about 4 mole percent. In one embodiment, the catalytic amount of the compound of formula (J) is from about 2 mole percent to about 4 mole percent. In one embodiment, the catalytic amount of the compound of formula (J) is from about 1 mole percent to about 2 mole percent. In one embodiment, the catalytic amount of the compound of formula (J) is about 1 mole percent or about 2 mole percent.

In some embodiments, in step (e) the tert-butoxide salt is selected from the group consisting of sodium tert-butoxide and potassium tert-butoxide. In some embodiments, in step (e) the tert-butoxide salt is sodium tert-butoxide. In some embodiments, in step (e) the tert-butoxide salt is potassium tert-butoxide.

In some embodiments, in step (e) the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, in step (e) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (e) the organic solvent is DMF.

In some embodiments, in step (f), $R^1$ is $C_1$ to $C_4$ alkyl. In some embodiments, $R^1$ is isopropyl.

In some embodiments, in step (f), R is methyl and the $C_1$ to $C_{12}$ alkyl chloroformate is methyl chloroformate. In some embodiments, R is ethyl and the $C_1$ to $C_{12}$ alkyl chloroformate is ethyl chloroformate. In some embodiments, R is tert-butyl and the di-($C_1$ to $C_{12}$ alkyl)dicarbonate is di-tert-butyl dicarbonate.

In some embodiments, in step (f) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (f) the aprotic organic solvent is THF.

In some embodiments, in step (i) the source of palladium is $Pd(OAc)_2$.

In some embodiments, in step (i) the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, in step (i) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (i) the organic solvent is acetonitrile.

In some embodiments, step (i) comprises combining tetrabutylammonium bromide with the compound of formula (F), a source of palladium and 4-chlorophenylboronic acid in the organic solvent.

In some embodiments, in step (j) the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, in step (j) the organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (j) the organic solvent is a mixture of THF and toluene. In some embodiments, the mixture of THF and toluene is about 1:1 by volume.

In some embodiments, step (j) further comprises producing the compound of formula (H) as a crystalline solid. In some embodiments, step (j) further comprises:

(1) adding an aqueous solution to the mixture of step (j) to produce an aqueous and an organic phase;
(2) separating the organic phase from the mixture of step (1);
(3) concentrating the organic phase; and
(4) adding an organic solvent to the mixture of step (3) to produce the compound of formula (H) as a crystalline solid.

In some embodiments of step (4) of step (j), the organic solvent is acetonitrile. In some embodiments of step (4) of step (j), the organic solvent is acetonitrile and the mixture is heated to about 80° C.

In some embodiments, step (4) of step (j) further comprises cooling the mixture to about 10° C. to about −10° C. In some embodiments, step (4) of step (j) further comprises cooling the mixture to about −10° C., and isolating the compound of formula (H) as a crystalline solid by filtering the mixture.

In some embodiments, the combining of step (k) is in an organic solvent. In some embodiments, the organic solvent is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, the organic solvent is isopropanol.

In some embodiments, step (k) further comprises producing the compound of formula (I) as a crystalline solid. In some embodiments, the combining of step (k) is in an organic solvent, and step (k) further comprises isolating the compound of formula (I) as a crystalline solid by filtering the mixture.

In some embodiments, the combining of step (k) is in an organic solvent, and step (k) further comprises cooling the mixture to about 10° C. to about −10° C. to produce the compound of formula (I) as a crystalline solid.

In some embodiments, the combining of step (k) is in isopropanol, and step (k) further comprises cooling the mixture to about 10° C. to about −10° C. to produce the compound of formula (I) as a crystalline solid. In some embodiments, the combining of step (k) is in isopropanol, and step (k) further comprises cooling the mixture to about −5° C. to produce the compound of formula (I) as a crystalline solid, and isolating the compound of formula (I) as a crystalline solid by filtering the mixture.

Also provided herein is a process of preparing a compound of formula (C):

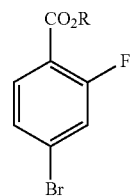

(C)

wherein R is $C_1$ to $C_{12}$ alkyl, which comprises
(a) combining a compound of formula (A):

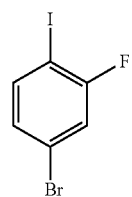

(A)

with $R^1$MgX in an aprotic organic solvent; wherein $R^1$ is $C_1$ to $C_6$ alkyl; and X is Cl, Br or I; and
(b) combining a $C_1$ to $C_{12}$ alkyl chloroformate or a di-($C_1$ to $C_{12}$ alkyl)dicarbonate with the product of step (a), to provide the compound of formula (C).

In some embodiments, R is $C_1$ to $C_6$ alkyl. In some embodiments, R is $C_1$ to $C_4$ alkyl. In some embodiments, R is selected from the group consisting of methyl, ethyl, n-propyl, isopropyl, n-butyl, tert-butyl, iso-butyl and neo-butyl. In some embodiments, R is tert-butyl.

In some embodiments, $R^1$ is $C_1$ to $C_4$ alkyl. In some embodiments, $R^1$ is isopropyl.

In some embodiments, the organic solvent of step (a) is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments the organic solvent of step (a) is THF.

In one embodiment, R is $C_1$ to $C_6$ alkyl.
In one embodiment, R is selected from the group consisting of methyl, ethyl, n-propyl, isopropyl, n-butyl, tert-butyl, iso-butyl and neo-butyl.
In one embodiment, R is selected from the group consisting of methyl, ethyl, n-propyl, isopropyl, n-butyl, tert-butyl, iso-butyl and neo-butyl; and $R^1$ is isopropyl.
In one embodiment, R is tert-butyl and $R^1$ is isopropyl.
In some embodiments, in step (b), R is methyl and the $C_1$ to $C_{12}$ alkyl chloroformate is methyl chloroformate. In some embodiments, R is ethyl and the $C_1$ to $C_{12}$ alkyl chloroformate is ethyl chloroformate. In some embodiments, R is tert-butyl and the di-($C_1$ to $C_{12}$ alkyl)dicarbonate is di-tert-butyl dicarbonate.

Also provided herein is a process for the preparation of a compound of formula (D):

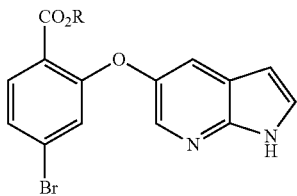

wherein R is $C_1$ to $C_{12}$ alkyl,
which comprises:

(x) combining a compound of formula (B):

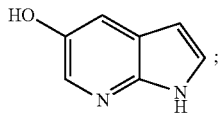

with a compound of formula (C):

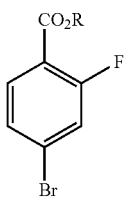

and a tert-butoxide salt in an organic solvent to provide the compound of formula (D).

In one embodiment, R is tert-butyl.

In some embodiments, the process of preparing the compound of formula (D) further comprises steps (x') and (x''):

(x') combining a compound of formula (A):

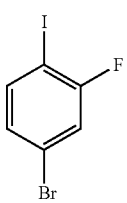

with $R^1MgX$ in an aprotic organic solvent; wherein $R^1$ is $C_1$ to $C_6$ alkyl; and X is Cl, Br or I;

(x'') combining a $C_1$ to $C_{12}$ alkyl chloroformate or a di-($C_1$ to $C_{12}$ alkyl)dicarbonate with the product of step (x'), to provide the compound of formula (C).

In some embodiments, in step (x) the tert-butoxide salt is selected from the group consisting of sodium tert-butoxide and potassium tert-butoxide.

In some embodiments, the organic solvent of step (x) is selected from the group consisting of pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, THF, DMF, HMPA, NMP, nitromethane, acetone, acetic acid, acetonitrile, ethyl acetate, diethyl ether, diethylene glycol, glyme, diglyme, petroleum ether, dioxane, MTBE, benzene, toluene, xylene, pyridine, 2-methyltetrahydrofuran, and mixtures thereof. In some embodiments, the organic solvent of step (x) is DMF.

In some embodiments, in step (x'), $R^1$ is a $C_1$ to $C_4$ alkyl. In some embodiments, $R^1$ is isopropyl.

In some embodiments, in step (x''), the $C_1$ to $C_{12}$ alkyl chloroformate is methyl chloroformate. In some embodiments, the $C_1$ to $C_{12}$ alkyl chloroformate is ethyl chloroformate. In some embodiments, the di-($C_1$ to $C_{12}$ alkyl)dicarbonate is di-tert-butyl dicarbonate.

In some embodiments, in step (x') the aprotic organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, in step (x') the aprotic organic solvent is THF.

Also provided herein is a compound of the formula (2):

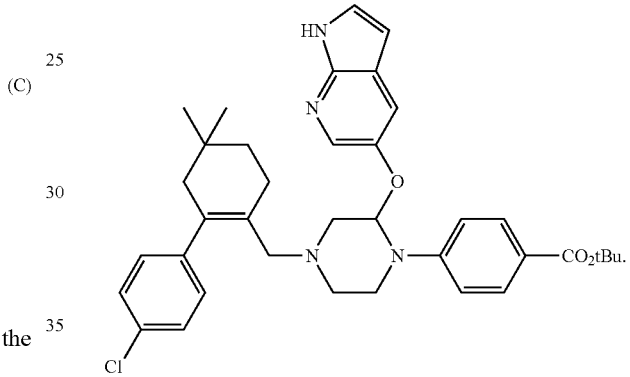

In one embodiment, the compound of the formula (2) is prepared by the following steps:

(y) combining a compound of formula (B):

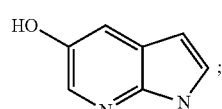

with a compound of formula (C):

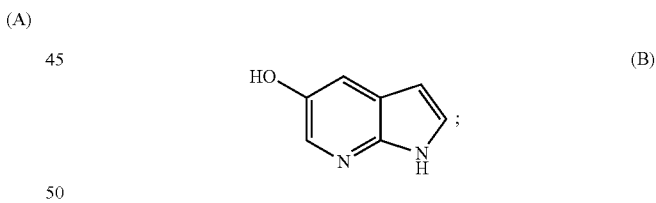

wherein R is tert-butyl,
and a tert-butoxide salt in an organic solvent to provide the compound of formula (D):

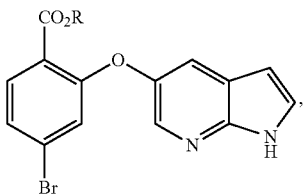

wherein R is tert-butyl; and (z) combining the compound of formula (D), wherein R is tert-butyl;

with a compound of formula (I):

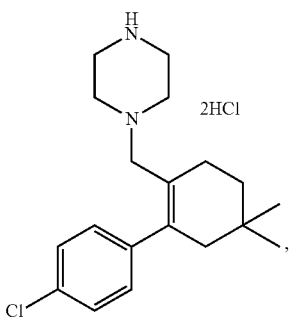

a source of palladium, a tert-butoxide salt, and a phosphine ligand in an aprotic organic solvent.

In one embodiment, the phosphine ligand of step (z) is a compound of formula (J):

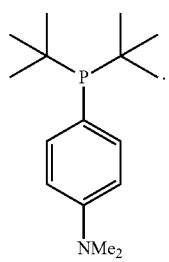

In one embodiment, in step (z) the source of palladium is $Pd_2dba_3$.

In some embodiments, in step (z) the aprotic organic solvent is selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, the aprotic organic solvent is a mixture of THF and toluene.

In some embodiments, in step (z), the tert-butoxide salt is selected from the group consisting of sodium tert-butoxide and potassium tert-butoxide.

In some embodiments, in step (z) the tert-butoxide salt is anhydrous sodium tert-butoxide or anhydrous potassium tert-butoxide.

In some embodiments, step (z) further comprises the following steps:

(1) combining the tert-butoxide salt with the compound of formula (I) in an aprotic organic solvent;

(2) combining the source of palladium, the compound of formula (J), and the compound of formula (D) in an aprotic organic solvent; and (3) adding the mixture of step (1) to the mixture of step (2).

In some embodiments, in step (z) the mixture resulting from step (2) is filtered prior to step (3).

In some embodiments, step (z) is carried out under an atmosphere of nitrogen or argon.

In some embodiments, in step (z) a catalytic amount of the source of palladium is used relative to the amount of compound (I). In some embodiments, the source of palladium is $Pd_2dba_3$ and the catalytic amount of $Pd_2dba_3$ is from about 0.5 mole percent to about 2 mole percent. In one embodiment, the catalytic amount of $Pd_2dba_3$ is about 0.75 mole percent.

In some embodiments, when the phosphine ligand of step (z) is a compound for formula (J), a catalytic amount of the compound of formula (J) is used relative to the amount of compound (I). In some embodiments, the catalytic amount of the compound of formula (J) is from about 1 mole percent to about 5 mole percent. In one embodiment, the catalytic amount of the compound of formula (J) is from about 1 mole percent to about 4 mole percent. In one embodiment, the catalytic amount of the compound of formula (J) is from about 2 mole percent to about 4 mole percent. In one embodiment, the catalytic amount of the compound of formula (J) is from about 1 mole percent to about 2 mole percent. In one embodiment, the catalytic amount of the compound of formula (J) is about 1 mole percent or about 2 mole percent.

In another embodiment, provided herein are compounds of the formulae:

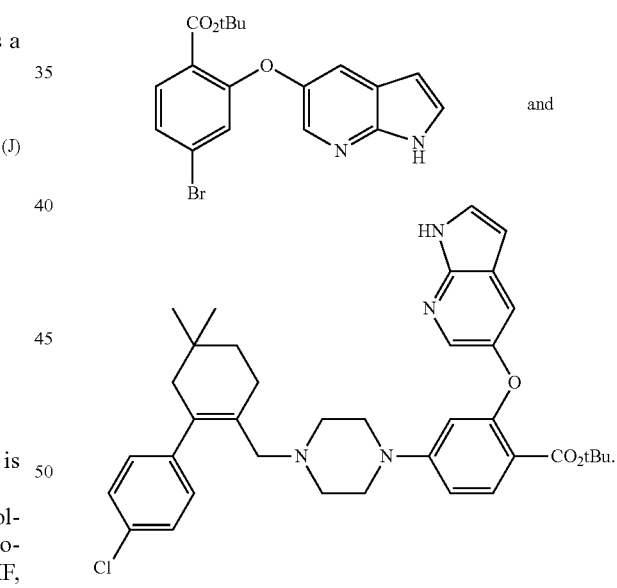

In some embodiments, the processes described herein are improved methods for commercial chemical manufacturing of Compound 1. Without being bound to a particular theory or mechanism of action, the processes described herein significantly improve the overall efficiency and product yield of Compound 1. Previous processes (e.g., U.S. Patent Publication Nos. 2010/0305122 and 2012/0157470, and International Patent Publication Nos. WO 2011/15096 and WO 2012/071336) were found to lack feasibility for production of Compound 1 on a commercial scale. Thus, the processes provided herein represent improved methods for the synthesis of Compound 1 in quantities required for clinical and/or commercial development. Improvements relative to these previous processes include, but are not limited to, overall yield of Compound 1, overall process efficiency and economics, mild reaction conditions, practical isolation/purification procedures, and viability for commercialization.

The improved process provided herein involves a selective nucleophilic aromatic substitution reaction ("SnAr reaction") of compounds (B) and (C), which can be carried out under milder conditions with a shorter reaction time when compared to previously described processes as found, for example, in U.S. Patent Publication Nos. 2010/0305122 and 2012/0157470, and International Patent Publication Nos. WO 2011/15096 and WO 2012/071336. Without being limited by theory, the improved SnAr reaction of compound (B) and (C) does not generate regioisomeric side products which necessitate further purification to remove the side products, as was the case in previously described processes. The SnAr reaction in the previous process also requires a longer reaction time and harsh reaction conditions which result in a low overall yield relative to the processes described herein. Furthermore, the previous processes also require tedious purification of the intermediates which is impracticable on a large, commercial scale process. The processes described herein are more convergent than prior processes, resulting in a highly efficient cross-coupling reaction of compound (D) and the free base of compound (I) in high yield. In some embodiments, the processes described herein utilize crystalline solid intermediates (H) and (I), which allow efficient purification by crystallization to remove impurities—advantages not available in previously described processes.

The following schemes illustrate one or more embodiments of the process provided herein. In some embodiments, the compound of formula (D) is prepared from compound (B) and compound (C) as shown in Scheme 1 below. The compound of formula (B) may be prepared by techniques known in the art, e.g., as shown in WO 2000/047212 and *J. Am. Chem. Soc.*, 1959, 81: 743-747. The compound of formula (C) may be prepared by techniques known in the art, e.g., as shown in WO 2006/059801 and *Tetrahedron Letters*, 2008, 49(12), 2034-2037; or as shown in Scheme 2.

reagent wherein $R^1$ is an alkyl group, and X is Cl, Br or I. The electrophilic acetylating reagent of Scheme 2 can be, but is not limited to, methyl or ethyl chloroformate or $BOC_2O$.

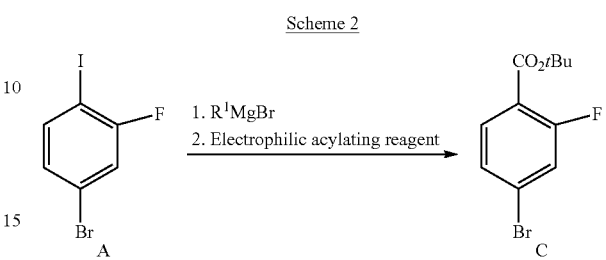

An exemplary reaction according to Scheme 2 is shown below.

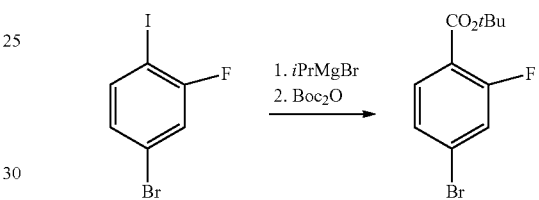

In another embodiment, the compound of formula (I) is prepared from compound (E) as shown in Scheme 3 below. Compound (E) is commercially available or may be prepared by techniques known in the art, e.g., as shown in U.S. Pat. No. 3,813,443 and *Proceedings of the Chemical Society, London*, 1907, 22, 302.

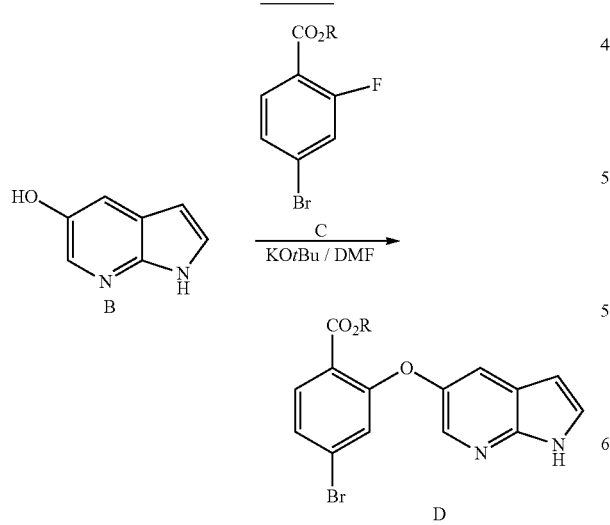

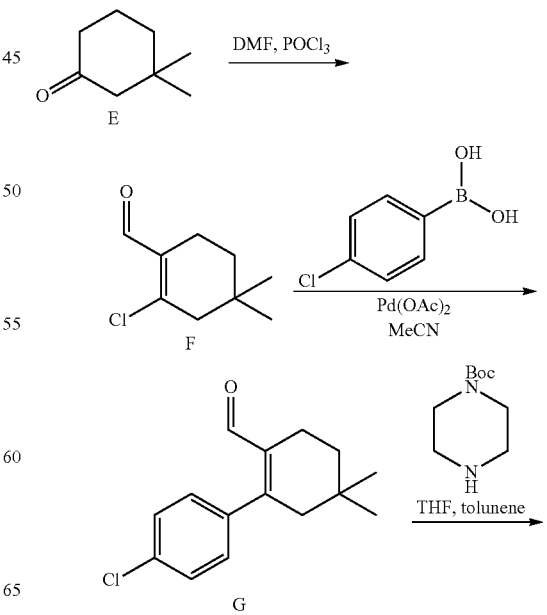

The compound of formula (C) of Scheme 1 may prepared from commercially available compound (A) as shown in Scheme 2 below, wherein "$R^1MgX$" represents a Grignard -continued

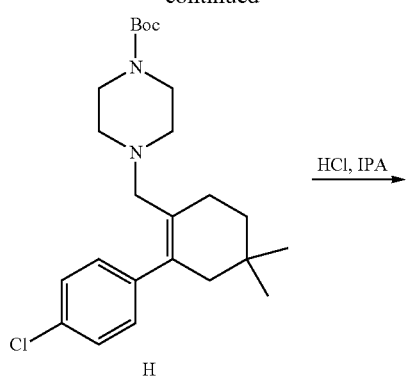

H

Scheme 5

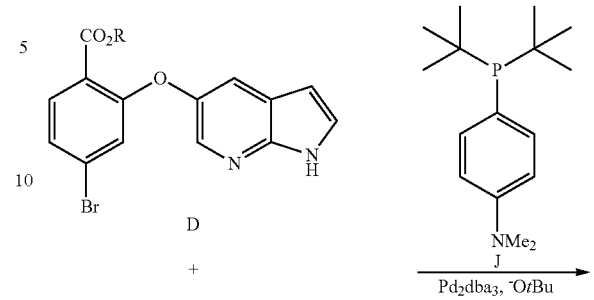

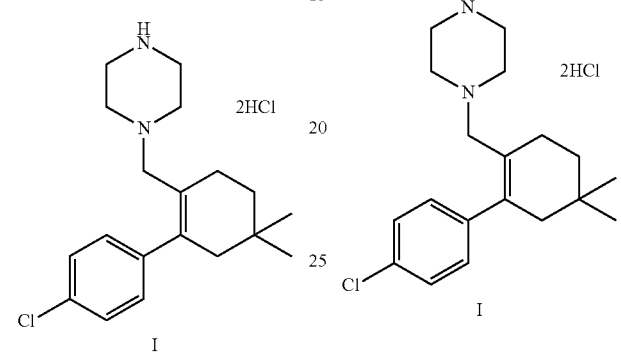

In another embodiment, the compound of formula (N) is prepared from compound (M) as shown in Scheme 4 below. Compound (M) is commercially available or may be prepared by techniques known in the art, e.g., as shown in GB 585940 and *J. Am. Chem. Soc.*, 1950, 72, 1215-1218.

Scheme 4

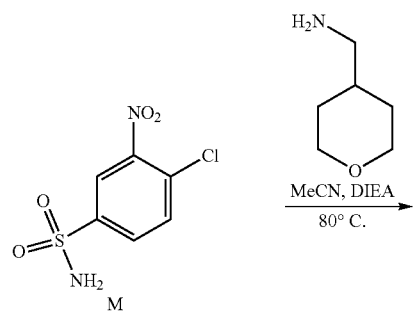

M

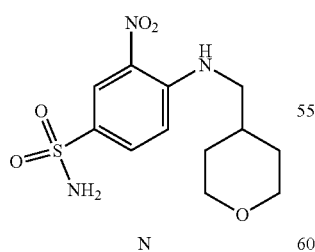

N

In another embodiment, the compound of formula (1) is prepared from compound (D) and compound (I) as shown in Scheme 5 below. Compound (J) may be prepared by techniques known in the art, e.g., as shown in WO 2009/117626 and Organometallics, 2008, 27(21), 5605-5611.

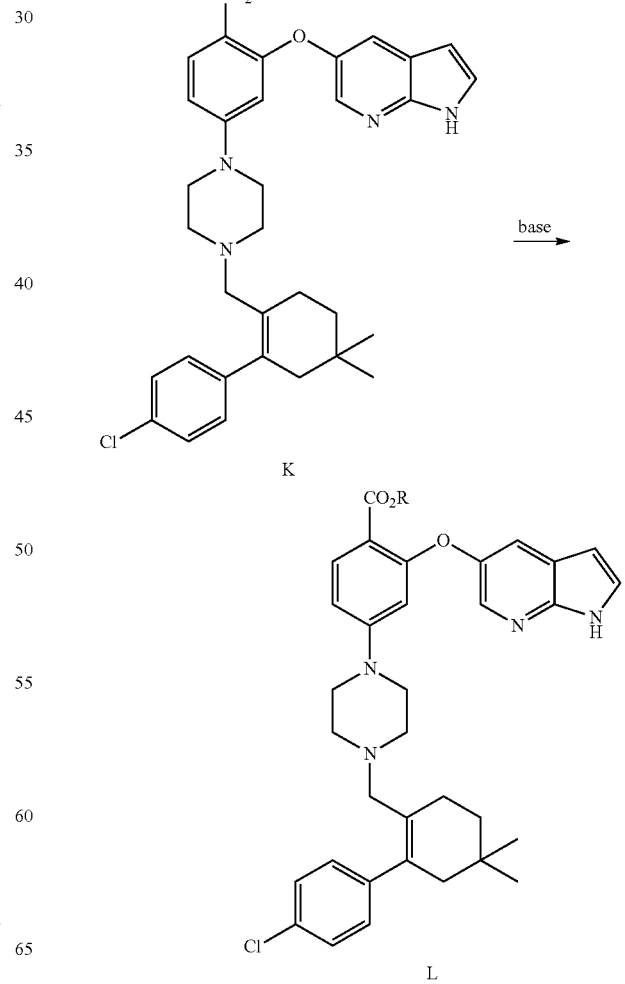

-continued

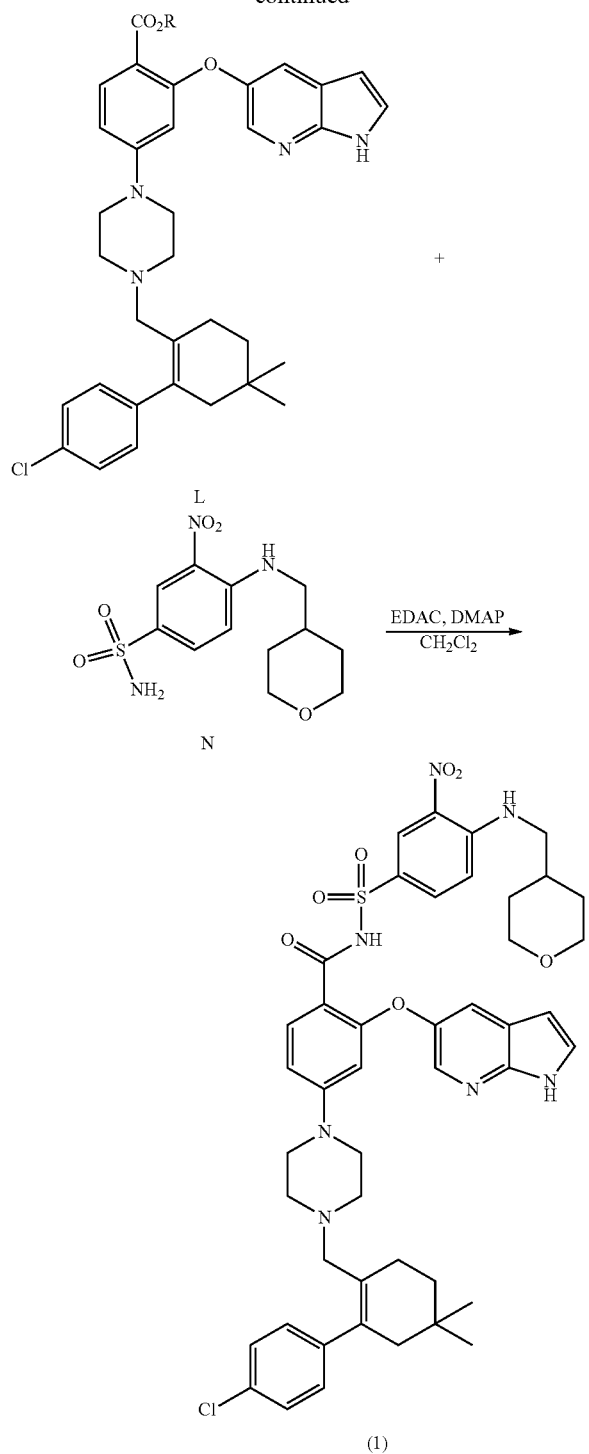

(1)

In some embodiments, the preparation of the compound of formula (K) from compound (D) and compound (I) is air and/or moisture sensitive, and is therefore performed under an inert atmosphere, e.g., using nitrogen or argon gas.

Without being bound to a particular theory, the use of compound (D) as an intermediate in the preparation of the compound of formula (1) as shown above in Schemes 1 to 5 is an improvement over previously described processes for the preparation of the compound of formula (1). In some embodiments, the improvements include higher product yields, shorter reaction times. In some embodiments, the improvements are provided when R is tert-butyl in compound (D).

Schemes 1 to 5 are non-limiting examples of the process provided herein. Solvents and/or reagents are known compounds and may be interchanged according to the knowledge of those skilled in the art.

Abbreviations used in Schemes 1 to 5 are as follows:

| Ac | acetyl |
|---|---|
| BOC | tert-butoxycarbonyl |
| dba | dibenzylidineacetone |
| DIEA | N,N-diisopropylethylamine |
| DMAP | 4-dimethylaminopyridine |
| DMF | dimethylformamide |
| EDAC | 1-ethyl-3-(3-dimethylaminopropyl)carbodiimide HCl |
| IPA | isopropanol |
| iPr | isopropyl |
| Me | methyl |
| n-Bu | n-butyl |
| tBu | tert-butyl |
| THF | tetrahydrofuran |

Unless indicated otherwise, the temperatures at which a reaction of Schemes 1 to 5 is conducted is not critical. In certain embodiments, when a temperature is indicated in a reaction, the temperature may be varied from about plus or minus 0.1° C., 0.5° C., 1° C., 5° C., or 10° C. Depending upon which solvent is employed in a particular reaction, the optimum temperature may vary. In some embodiments, reactions are conducted in the presence of vigorous agitation sufficient to maintain an essentially uniformly dispersed mixture of the reactants.

In conducting a reaction provided herein, neither the rate, nor the order, of addition of the reactants is critical unless otherwise indicated. Unless otherwise indicated, reactions are conducted at ambient atmospheric pressure. Unless otherwise indicated, the exact amount of reactants is not critical. In some embodiments, the amount of a reactant may be varied by about 10 mole percent or about 10% by weight.

Unless otherwise indicated, the organic solvents used in the processes provided herein may be selected from those commercially available or otherwise known to those skilled in the art. Appropriate solvents for a given reaction are within the knowledge of the skilled person and include mixtures of solvents. Examples of organic solvents provided herein for use include but are not limited to: pentane, hexane, heptane, cyclohexane, methanol, ethanol, 1-propanol, isopropanol, 1-butanol, 2-butanol, tert-butanol, 2-butanone, dichloromethane, chloroform, carbon tetrachloride, 1,2-dichloroethane, tetrahydrofuran (THF), dimethylformamide (DMF), hexamethylphosphoramide (HMPA), N-methyl-2-pyrrolidinone (NMP), nitromethane, acetone, acetic acid, acetonitrile, ethyl acetate, diethyl ether, diethylene glycol, glyme, diglyme, petroleum ether, dioxane, methyl tert-butyl ether (MTBE), benzene, toluene, xylene, pyridine, 2-methyltetrahydrofuran, and mixtures thereof In some embodiments, an organic solvent used in the processes provided herein is an aprotic organic solvent. As provided herein, an aprotic solvent is a solvent that does not contain an acidic hydrogen atom or a hydrogen atom that is capable of hydrogen bonding (e.g., is not bound to an oxygen or a nitrogen atom). The aprotic organic solvent may be selected from the group consisting of dichloromethane, chloroform, acetone, acetonitrile, THF, DMF, NMP, HMPA, dioxane, nitromethane, pyridine, 2-methyltetrahydrofuran, and mixtures thereof. In some embodiments, the aprotic organic solvent is THF. In some embodiments, the aprotic organic solvent is DMF. In some embodiments, the aprotic organic solvent is acetonitrile.

As provided herein, a "tertiary amine base" refers to an amine that is substituted with three alkyl groups, e.g., triethylamine or N,N-diisopropylethylamine As provided herein, a "catalytic amount" refers to less than one molar equivalent of a reagent or reactant in a given reaction, as determined relative to another reagent or reactant in the reaction mixture. In some embodiments, a catalytic amount is described as a mole percent relative to another reagent or reactant in the reaction mixture.

As provided herein, a "source of palladium" refers to a source of palladium in a stable oxidation state, i.e., Pd(0), Pd(I), Pd(II) and/or Pd(IV). The palladium may be free metal, such as in a powder form, or may be bound to one or more ligands, e.g., $PdCl_2$, $Pd_2dba_3$, $PdCl_2(PPh_3)_2$, $Pd(PPh_3)_4$, $Pd(OAc)_2$ or $[(cinnamyl)PdCl]_2$.

As provided herein, a "phosphine ligand" refers to a compound of formula $PR'_3$, wherein each R' is independently selected from $C_1$ to $C_6$ alkyl or phenyl, wherein the aryl group is optionally substituted by $C_1$ to $C_6$ alkyl, phenyl, trialkylamino, alkoxy or halo.

As provided herein, unless otherwise defined, the term "about" means that the value or amount to which it refers can vary by ±5%, ±2%, or ±1%.

The products obtained by any of the processes provided herein may be recovered by conventional means, such as evaporation or extraction, and may be purified by standard procedures, such as distillation, recrystallization or chromatography

EXAMPLES

Compounds of the following examples are shown in Schemes 1 to 5 above and were named using Chemdraw® Ultra software. In addition to the abbreviations described above with respect to the schemes provided herein, the following abbreviations are used in the Examples:

"HPLC"=high pressure liquid chromatography; "IP"=in process; "ML"=mother liquor; "NLT"=no less than; "NMT"=no more than; "RB"=round bottom; "RT"=room temperature; "sm"=starting material.

Unless indicated otherwise, compounds were characterized by HPLC and $^1$H NMR analysis and used in later reactions with or without purification. $^1$H NMR analysis was performed at 400 MHz unless otherwise indicated. Unless specified otherwise, product yield/purity was determined by weight, qNMR, and/or HPLC analysis.

Example 1

Synthesis of tert-butyl 4-bromo-2-fluorobenzoate (Compound (C))

To a 100 ml jacketed reactor equipped with a mechanical stirrer was charged 4-bromo-2-fluorol-iodobenzene, "Compound (A)" (5 g, 1.0 eq) and THF (25 ml). The solution was cooled to −5° C. 2 M isopropyl magnesium chloride in THF (10.8 ml, 1.3 eq) was slowly added maintaining the internal temperature below 0° C. The mixture was stirred at 0° C. for 1 h. Di-tert-butyl dicarbonate (5.44 g, 1.5 eq) in THF (10 ml) was added. After 1 h, the solution was quenched with 10% citric acid (10 ml), and then diluted with 25% NaCl (10 ml). The layers were separated and the organic layer was concentrated to near dryness and chased with THF (3×10 ml). The crude oil was diluted with THF (5 ml), filtered to remove inorganics, and concentrated to dryness. The crude oil (6.1 g, potency=67%, potency adjusted yield=88%) was taken to the next step without further purification. $^1$H NMR (DMSO-$d_6$): δ 1.53 (s, 9H), 7.50-7.56 (m, 1H), 7.68 (dd, J=10.5, 1.9 Hz, 1H), 7.74 (t, J=8.2 Hz, 1H).

Example 2

Synthesis of tert-butyl 2-((1H-pyrrolo[2,3-b]pyridin-5-yl)oxy)-4-bromobenzoate (Compound (D))

To a 3 L three-neck Morton flask were charged 1H-pyrrolo [2,3-b]pyridin-5-ol (80.0 g, 1.00 eq.), tert-butyl 4-bromo-2-fluorobenzoate (193 g, 1.15 eq.), and anhydrous DMF (800 mL). The mixture was stirred at 20° C. for 15 min. The resulting solution was cooled to about zero to 5° C. A solution of sodium tert-butoxide (62.0 g) in DMF (420 mL) was added slowly over 30 min while maintaining the internal temperature at NMT 10° C., and rinsed with DMF (30 mL). The reaction mixture was stirred at 10° C. for 1 hour (an off-white slurry) and adjusted the internal temperature to ~45° C. over 30 min. The reaction mixture was stirred at 45-50° C. for 7 hr and the reaction progress monitored by HPLC (IP samples: 92% conversion % by HPLC). The solution was cooled to ~20° C. The solution was stirred at 20° C. overnight.

Water (1200 mL) was added slowly to the reaction mixture at <30° C. over 1 hour (slightly exothermic). The product slurry was adjusted to ~20° C., and mixed for NLT 2 hours. The crude product was collected by filtration, and washed with water (400 mL). The wet-cake was washed with heptane (400 mL) and dried under vacuum at 50° C. overnight to give the crude product (236.7 g).

Re-crystallization or Re-slurry: 230.7 g of the crude product, (potency adjusted: 200.7 g) was charged back to a 3 L three-neck Morton flask. Ethyl acetate (700 mL) was added, and the slurry heated slowly to refluxing temperature over 1 hr (small amount of solids left). Heptane (1400 mL) was added slowly, and the mixture adjusted to refluxing temperature (78° C.). The slurry was mixed at refluxing temperature for 30 min., and cooled down slowly to down to ~−10° C. at a rate of approximate 10° C./hour, and mixed for 2 hr. The product was collected by filtration, and rinsed with heptane (200 ml).

The solid was dried under vacuum at ~50° C. overnight to give 194.8 g, 86% isolated yield of the product as an off-white solid. MS-ESI 389.0 (M+1); mp: 190-191° C. (uncorrected). $^1$H NMR (DMSO-$d_6$): δ 1.40 (s, 9H), 6.41 (dd, J=3.4, 1.7 Hz, 1H), 7.06 (d, J=1.8 Hz, 1H), 7.40 (dd, J=8.3, 1.8 Hz, 1H), 7.51 (t, J=3.4 Hz, 1H), 7.58 (d, J=2.6 Hz, 1H), 7.66 (d, J=8.3 Hz, 1H), 8.03 (d, J=2.7 Hz, 1H), 11.72 (s, 1H, NH).

Example 3

Synthesis of 2-chloro-4,4-dimethylcyclohexanecarbaldehyde (Compound (F))

To a 500 mL RB flask were charged anhydrous DMF (33.4 g, 0.456 mol) and $CH_2Cl_2$ (80 mL). The solution was cooled down <−5° C., and $POCl_3$ (64.7 g, 0.422 mol) added slowly over 20 min @<20° C. (exothermic), rinsed with $CH_2Cl_2$ (6 mL). The slightly brown solution was adjusted to 20° C. over 30 mM, and mixed at 20° C. for 1 hour. The solution was cooled back to <5° C. 3,3-Dimethylcyclohexanone (41.0 g, 90%, ~0.292 mol) was added, and rinsed with in $CH_2Cl_2$ (10 mL) (slightly exothermic) at <20° C. The solution was heated to refluxing temperature, and mixed overnight (21 hours.).

To a 1000 mL three neck RB flask provided with a mechanical stirrer were charged 130 g of 13.6 wt % sodium acetate trihydrate aqueous solution, 130 g of 12% brine, and 130 mL of $CH_2Cl_2$. The mixture was stirred and cooled down to <5° C. The above reaction mixture (clear and brown) was transferred, quenched into it slowly while maintaining the internal temperature <10° C. The reaction vessel was rinsed with $CH_2Cl_2$ (10 mL). The quenched reaction mixture was stirred at <10° C. for 15 min. and allowed to rise to 20° C. The mixture was stirred 20° C. for 15 min and allowed to settle for 30 min. (some emulsion). The lower organic phase was separated. The upper aq. phase was back extracted with $CH_2Cl_2$ (50 mL). The combined organic was washed with a mixture of 12% brine (150 g)-20% $K_3PO_4$ aq. solution (40 g). The organic was dried over $MgSO_4$, filtered and rinsed with $CH_2Cl_2$ (30 ml). The filtrate was concentrated to dryness under vacuum to give a brown oil (57.0 g, potency=90.9 wt % by qNMR, ~100%). $^1$H NMR ($CDCl_3$): δ 0.98 (s, 6H), 1.43 (t, J=6.4 Hz, 2H), 2.31 (tt, J=6.4, 2.2 Hz, 2H), 2.36 (t, J=2.2 Hz, 2H), 10.19 (s, 1H).

Example 4

Synthesis of 2-(4-chlorophenyl)-4,4-dimethylcyclohex-1-enecarbaldehyde (Compound (G))

To a 250 mL pressure bottle were charged 2-chloro-4,4-dimethylcyclohex-1-enecarbaldehyde (10.00 g), tetrabutylammonium bromide (18.67 g), and acetonitrile (10 mL). The mixture was stirred at 20° C. for 5 min. 21.0 wt % $K_2CO_3$ aq. solution (76.0 g) was added. The mixture was stirred at room temperature (rt) for NLT 5 min. followed by addition of 4-chlorophenylboronic acid (9.53 g) all at once. The mixture was evacuated and purged with $N_2$ for three times. Palladium acetate (66 mg, 0.5 mol %) was added all at once under $N_2$. The reaction mixture was evacuated and purged with $N_2$ for three times (an orange colored mixture). The bottle was back filled with $N_2$ and heated to ~35° C. in an oil bath (bath temp ~35° C.). The mixture was stirred at 30° C. overnight (15 hours). The reaction mixture was cooled to RT, and pulled IP sample from the upper organic phase for reaction completion, typically starting material <2% (orange colored mixture). Toluene (100 mL) and 5% $NaHCO_3$-2% L-Cysteine aq. solution (100 mL) were added. The mixture was stirred at 20° C. for 60 min. The mixture was filtered through a pad of Celite to remove black solid, rinsing the flask and pad with toluene (10 mL). The upper organic phase was washed with 5% $NaHCO_3$ aq. solution-2% L-Cysteine (100 mL) once more. The upper organic phase was washed with 25% brine (100 mL). The organic layer (105.0 g) was assayed (118.8 mg/g, 12.47 g product assayed, 87% assayed yield), and concentrated to ~1/3 volume (~35 mL). The product solution was directly used in the next step without isolation. However, an analytical sample was obtained by removal of solvent to give a brown oil. $^1$HNMR ($CDCl_3$): δ 1.00 (s, 6H), 1.49 (t, J=6.6 Hz, 2H), 2.28 (t, J=2.1 Hz, 2H), 2.38 (m, 2H), 7.13 (m, 2H), 7.34 (m, 2H), 9.47 (s, 1H).

Example 5

Synthesis of tert-butyl 4-((4'-chloro-5,5-dimethyl-3,4,5,6-tetrahydro-[1,1'-biphenyl]-2-yl)methyl)piperazine-1-carboxylate (Compound (H))

To a 2 L three neck RB flask provided with a mechanical stirrer were charged a solution of 4'-chloro-5,5-dimethyl-3,4,5,6-tetrahydro-[1,1'-biphenyl]-2-carbaldehyde (50.0 g) in toluene (250 mL), BOC-piperazine (48.2 g) and anhydrous THF (250 mL). The yellow solution was stirred at 20° C. for 5 min. Sodium triacetoxyborohydride (52.7 g) was added in portion (note: the internal temperature rose to ~29.5° C. in 15 min cooling may be needed). The yellow mixture was stirred at ~25° C. for NLT 4 hrs. A conversion of starting material to product of 99.5% was observed by HPLC after a 3 hour reaction time.

12.5 wt % brine (500 g) was added slowly to quench the reaction. The mixture was stirred at 20° C. for NLT 30 min and allowed to settle for NLT 15 min. The lower aq. phase (~560 mL) was separated (note: leave any emulsion in the upper organic phase). The organic phase was washed with 10% citric acid solution (500 g×2). 500 g of 5% $NaHCO_3$ aq. solution was charged slowly into the flask. The mixture was stirred at 20° C. for NLT 30 min., and allowed to settle for NLT 15 min. The upper organic phase was separated. 500 g of 25% brine aq. solution was charged. The mixture was stirred at 20° C. for NLT 15 min., and allowed to settle for NLT 15 min. The upper organic phase was concentrated to ~200 mL volume under vacuum. The solution was adjusted to ~30° C., and filtered off the inorganic salt. Toluene (50 mL) was used as a rinse. The combined filtrate was concentrated to ~100 mL volume. Acetonitrile (400 mL) was added, and the mixture heated to ~80° C. to achieve a clear solution. The solution was cooled down slowly to 20° C. slowly at rate 10° C./hour, and mixed at 20° C. overnight (the product is crystallized out at ~45-50° C., if needed, seed material may be added at 50° C.). The slurry was continued to cool down slowly to ~-10° C. at rate of 10° C./hours. The slurry was mixed at ~-10° C. for NLT 6 hours. The product was collected by filtration, and rinsed with pre-cooled acetonitrile (100 mL). The solid was dried under vacuum at 50° C. overnight (72.0 g, 85%). MS-ESI: 419 (M+1); mp: 109-110° C. (uncorrected); $^1$H NMR ($CDCl_3$): δ 1.00 (s, 6H), 1.46 (s, 9H), 1.48 (t, J=6.5 Hz, 2H), 2.07 (s, br, 2H), 2.18 (m, 4H), 2.24 (t, J=6.4 Hz, 2H), 2.80 (s, 2H), 3.38 (m, 4H), 6.98 (m, 2H), 7.29 (m, 2H).

Example 6

Synthesis of 1-((4'-chloro-5,5-dimethyl-3,4,5,6-tetrahydro-[1,1'-biphenyl]-2-yl)methyl)piperazine dihydrochloride (Compound (I))

To a 2.0 L three-neck RB flask equipped with a mechanical stirrer were charged the Boc reductive amination product (Compound (H), 72.0 g) and IPA (720 mL). The mixture was stirred at rt for 5 min, and 59.3 g of concentrated hydrochloride aq. solution added to the slurry. The reaction mixture was adjusted to an internal temperature of ~65° C. (a clear and colorless solution achieved). The reaction mixture was agitated at ~65° C. for NLT 12 hours.

The product slurry was cooled down to -5° C. slowly (10° C./hour). The product slurry was mixed at ~-5° C. for NLT 2 hours, collected by filtration. The wet cake was washed with IPA (72 mL) and dried at 50° C. under vacuum overnight to give 73.8 g (95%) of the desired product as a bis-hydrochloride IPA solvate (purity >99.5% peak area at 210 nm). MS-ESI: 319 (M+1); $^1$HNMR ($D_2O$): δ1.00 (s, 6H), 1.19 (d, J=6.0 Hz, 6H, IPA), 1.65 (t, J=6.1 Hz, 2H), 2.14 (s, br, 2H), 2.26 (m, 2H), 3.36 (br, 4H), 3.55 (s, br, 4H), 3.82 (s, 2H), 4.02 (septet, J=6.0 Hz, 1H, IPA), 7.16 (d, J=8.1 Hz, 2H), 7.45 (d, J=8.1 Hz, 2H; $^1$HNMR ($CDCl_3$): δ 0.86 (s, 6H), 1.05 (d, J=6.0 Hz, 6H, IPA), 1.42 (t, J=6.1 Hz, 2H), 2.02 (s, br, 2H), 2.12 (m, 2H), 3.23 (m, 4H), 3.4 (s, br, 4H), 3.68 (s, 2H), 3.89 (septet, J=6.0 Hz, 1H, IPA), 7.11 (d, J=8.1 Hz, 2H), 7.41 (d, J=8.1 Hz, 2H).

Example 7

Synthesis of 3-nitro-4-(((tetrahydro-2H-pyran-4-yl)methyl)amino)-benzenesulfonamide (Compound (N))

To a 500 mL three-neck RB flask equipped with a mechanical stirrer were charged the 4-chloro-3-nitrobenzenesulfonamide, Compound M (10.0 g), diisopropylethylamine (17.5 g), (tetrahydro-2H-pyran-4-yl)methanamine (7.0 g) and acetonitrile (150 mL). The reaction mixture was adjusted to an internal temperature of 80° C. and agitated for no less than 12 hours.

The product solution was cooled down to 40° C. and agitated for no less than 1 hour until precipitation observed. The product slurry was further cooled to 20° C. Water (75 mL) was slowly charged over no less than 1 hour, and the mixture cooled to 10° C. and agitated for no less than 2 hours before collected by filtration. The wet cake was washed with 1:1 mix of acetonitrile:water (40 mL). The wet cake was then reslurried in water (80 mL) at 40° C. for no less than 1 hour before collected by filtration. The wet cake was rinsed with water (20 mL), and dried at 75° C. under vacuum to give 12.7 g of the desired product in 99.9% purity and in 91% weight-adjusted yield. $^1$H NMR (DMSO-d$_6$): δ 1.25 (m, 2H), 1.60 (m, 2H), 1.89 (m, 1H), 3.25 (m, 2H), 3.33 (m, 2H), 3.83 (m, 2H), 7.27 (d, J=9.3 Hz, 1H), 7.32 (s, NH$_2$, 2H), 7.81 (dd, J=9.1, 2.3 Hz, 1H), 8.45 (d, J=2.2 Hz, 1H), 8.54 (t, J=5.9 Hz, 1H, NH).

Example 8

Synthesis of tert-butyl 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl) benzoate (Compound (K))

General Considerations:

this chemistry is considered air and moisture sensitive. While the catalyst precursors in their solid, dry form can be handled and stored in air without special precautions, contact with even small amounts of solvent may render them susceptible to decomposition. As a result, traces of oxygen or other competent oxidants (e.g., solvent peroxides) must be removed prior to combination of the catalyst precursors with solvent and care must be used to prevent ingress of oxygen during the reaction. Also, care must be taken to use dry equipment, solvents, and reagents to prevent formation of undesirable byproducts. The sodium t-butoxide used in this reaction is hygroscopic and it should be properly handled and stored prior to or during use.

To a 2.0 L three-neck RB flask equipped with a mechanical stirrer were charged the bis-hydrochloride salt (Compound (I), 42.5 g) and toluene (285 ml). 20% K$_3$PO$_4$ (285 ml) was added and the biphasic mixture was stirred for 30 min. The layers were separated and the organic layer was washed with 25% NaCl (145 ml). The organic layer concentrated to 120 g and used in the coupling reaction without further purification.

NaOtBu (45.2 g) and Compound (I) in toluene solution (120 g solution-30 g potency adjusted) were combined in THF (180 ml) in a suitable reactor and sparged with nitrogen for NLT 45 min. Pd$_2$dba$_3$ (0.646 g), Compound (J) (0.399 g), and Compound (D) (40.3 g) were combined in a second suitable reactor and purged with nitrogen until oxygen level was NMT 40 ppm. Using nitrogen pressure, the solution containing Compound (I) and NaOtBu in toluene/THF was added through a 0.45 μm inline filter to the second reactor (catalyst, Compound (J) and Compound (D)) and rinsed with nitrogen sparged THF (30 ml.).

The resulting mixture was heated to 55° C. with stirring for NLT 16 h, then cooled to 22° C. The mixture was diluted with 12% NaCl (300 g) followed by THF (300 ml). The layers were separated.

The organic layer was stirred with a freshly prepared solution of L-cysteine (15 g), NaHCO$_3$ (23 g), and water (262 ml). After 1 h the layers were separated.

The organic layer was stirred with a second freshly prepared solution of L-cysteine (15 g), NaHCO$_3$ (23 g), and water (262 ml). After 1 h the layers were separated. The organic layer was washed with 12% NaCl (300 g), then filtered through a 0.45 μm inline filter. The filtered solution was concentrated in vacuo to ~300 mL, and chased three times with heptane (600 mL each) to remove THF.

The crude mixture was concentrated to 6 volumes and diluted with cyclohexane (720 ml). The mixture was heated to 75° C., held for 15 min, and then cooled to 65° C. over NLT 15 min. Seed material was charged and the mixture was held at 65° C. for 4 hours. The suspension was cooled to 25° C. over NLT 8 h, then held at 25° C. for 4 hours. The solids were filtered and washed with cyclohexane (90 ml) and dried at 50° C. under vacuum.

Isolated 52.5 g (88.9% yield) as a white solid. Melting point (uncorrected) 154-155° C. $^1$H NMR (DMSO-d$_6$): δ 0.93 (s, 6H), 1.27 (s, 9H), 1.38 (t, J=6.4 Hz, 2H), 1.94 (s, 2H), 2.08-2.28 (m, 6H), 2.74 (s, 2H), 3.02-3.19 (m, 4H), 6.33 (dd, J=3.4, 1.9 Hz, 1H), 6.38 (d, J=2.4 Hz, 1H), 6.72 (dd, J=9.0, 2.4 Hz, 1H), 6.99-7.06 (m, 2H), 7.29 (d, J=2.7 Hz, 1H), 7.30-7.36 (m, 2H), 7.41-7.44 (m, 1H), 7.64 (t, J=6.7 Hz, 1H), 7.94 (d, J=2.7 Hz, 1H), 11.53 (s, 1H).

Example 9

Synthesis of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (Compound (L))

Solution preparation: 10% KH$_2$PO$_4$ (aq): KH$_2$PO$_4$ (6 g) in water (56 g); 2:1 heptane/2-MeTHF: heptane (16 mL) in 2-MeTHF (8 mL).

Compound (K) (5.79 g), potassium tert-butoxide (4.89 g), 2-methyltetrahydrofuran (87 mL), and water (0.45 mL) were combined in a suitable reactor under nitrogen and heated to 55° C. until reaction completion. The reaction mixture was cooled to 22° C., washed with the 10% KH$_2$PO$_4$ solution (31 g) twice. The organic layer was then washed with water (30 g).

After removal of the aqueous layer, the organic layer was concentrated to 4 volumes (~19 mL) and heated to no less than 50° C. Heptane (23 ml) was slowly added. Alternatively, after removal of the aqueous layer, the organic layer was concentrated to 5 volumes and heated to no less than 70° C. and 5 volumes of heptane were slowly added. The resulting suspension was cooled to 10° C. Solids were then collected by vacuum filtration with recirculation of the liquors and the filter cake washed with 2:1 heptane/2-MeTHF (24 ml). Drying of the solids at 80° C. under vacuum yielded 4.0 g of Compound (L) in approximately 85% weight-adjusted yield. $^1$H NMR (DMSO-d$_6$): δ 0.91 (s, 6H), 1.37 (t, J=6.4 Hz, 2H), 1.94 (s, br, 2H), 2.15 (m, 6H), 2.71 (s, br, 2H), 3.09 (m, 4H), 6.31 (d, J=2.3 Hz, 1H), 6.34 (dd, J=3.4, 1.9 Hz, 1H), 6.7 (dd, J=9.0, 2.4 Hz, 1H), 7.02 (m, 2H), 7.32 (m, 2H), 7.37 (d, J=2.6 Hz, 1H), 7.44 (t, J=3.0 Hz, 1H), 7.72 (d, J=9.0 Hz, 1H), 7.96 (d, J=2.7 Hz, 1H) & 11.59 (m, 1H).

Example 10

Synthesis of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (Compound (1))

Solution preparation prior to reaction: 10% Acetic Acid: Acetic Acid (37 mL) in water (333 g); 5% NaHCO$_3$: NaHCO$_3$ (9 g) in water (176 g); 5% NaCl:NaCl (9 g) in water (176 g).

Compound (N) (13.5 g), DMAP (10.5 g), EDAC (10.7 g) and dichloromethane (300 mL) were combined in a suitable reactor and agitated at 25° C. In a second suitable reactor was charged the Acid (Compound (L), 25 g), $Et_3N$ (8.7 g) and dichloromethane (120 mL). The resulting Acid (Compound (L)) solution was slowly charged to the initial suspension of Compound (N) and agitated until reaction completion. N,N-dimethylethylenediamine (9.4 g) was then charged to the reaction mixture with continued agitation. The reaction mixture was warmed to 35° C. and washed with 10% Acetic acid solution (185 mL) twice. The lower organic layer was diluted with more dichloromethane (75 mL) and methanol (12.5 mL). The organic, product layer was then washed with 5% $NaHCO_3$ solution (185 mL) and then washed with 5% NaCl solution (185 mL) at 35° C. The lower, organic layer was separated and then concentrated to 8 vol (~256 mL) diluted with methanol (26 mL) and warmed to 38° C. Ethyl Acetate (230 mL) was slowly charged. The resulting suspension was slowly cooled to 10° C. and then filtered. The wet cake was washed twice with a 1:1 mix of dichloromethane and ethyl acetate (~2 vol, 64 mL). After drying the wet cake at 90° C., 32 g (84%) of Compound (1) was isolated. $^1$H NMR (DMSO-$d_6$): δ 0.90 (s, 6H), 1.24 (m, 2H), 1.36 (t, J=6.4 Hz, 2H), 1.60 (m, 2H), 1.87 (m, 1H), 1.93 (s, br, 2H), 2.12 (m, 2H), 2.19 (m, 4H), 2.74 (s, br, 2H), 3.06 (m, 4H), 3.26 (m, 4H), 3.83 (m, 2H), 6.17 (d, J=2.1 Hz, 1H), 6.37 (dd, J=3.4, 1.9 Hz, 1H), 6.66 (dd, J=9.1, 2.2 Hz, 1H), 7.01 (m, 2H), 7.31 (m, 2H), 7.48 (m, 3H), 7.78 (dd, J=9.3, 2.3 Hz, 1H), 8.02 (d, J=2.61 Hz, 1H), 8.54 (d, J=2.33 Hz, 1H), 8.58 (t, J=5.9 Hz, 1H, NH), 11.65 (m, 1H).

All references cited herein are incorporated by reference in their entirety. While the methods provided herein have been described with respect to the particular embodiments, it will be apparent to those skilled in the art that various changes and modifications can be made without departing from the spirit and scope as recited by the appended claims.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A process for the preparation of a compound of formula (C):

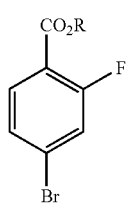

(C)

wherein R is $C_1$ to $C_{12}$ alkyl, which comprises:
(a) combining a compound of formula (A):

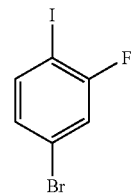

(A)

with $R^1MgX$ in an aprotic organic solvent; wherein $R^1$ is $C_1$ to $C_6$ alkyl and X is Cl, Br or I; and
(b) combining a $C_1$ to $C_{12}$ alkyl chloroformate or a di-($C_1$ to $C_{12}$ alkyl)dicarbonate with the product of step (a), to provide the compound of formula (C).

2. The process of claim 1 wherein R is selected from the group consisting of methyl, ethyl, n-propyl, isopropyl, n-butyl, tert-butyl, iso-butyl and neo-butyl.

3. The process of claim 1 wherein $R^1$ is isopropyl.

4. The process of claim 1 wherein R is ethyl and the $C_1$ to $C_{12}$ alkyl chloroformate is ethyl chloroformate.

5. The process of claim 1 wherein R is tert-butyl and the di-($C_1$ to $C_{12}$ alkyl)dicarbonate is di-tert-butyl dicarbonate.

6. A compound of the formula:

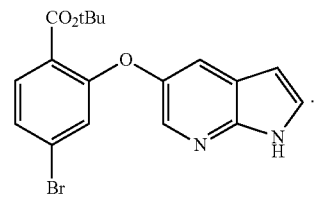 [SMILES: CC(C)(C)OC(=O)c1ccc(Br)cc1Oc1cnc2[nH]ccc2c1]

7. A process for the preparation of the compound of claim 6, wherein the process comprises:
(x) combining a compound of formula (B):

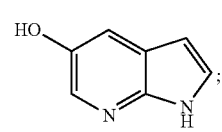

(B)

with a compound of formula (C):

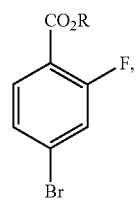

(C)

wherein R is tert-butyl,
and a tert-butoxide salt in an organic solvent to provide the compound of claim 6.

8. A compound of the formula:

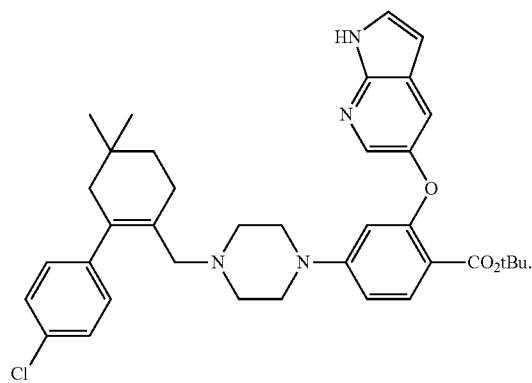 [SMILES: CC1(C)CCC(CN2CCN(c3ccc(C(=O)OC(C)(C)C)c(Oc4cnc5[nH]ccc5c4)c3)CC2)=C(c2ccc(Cl)cc2)C1]

9. A process for the preparation of the compound of claim 8, wherein the process comprises:
(y) combining a compound of formula (B):

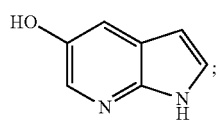
(B)

with a compound of formula (C):

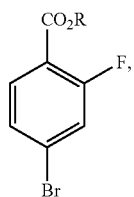
(C)

wherein R is tert-butyl, and a tert-butoxide salt in an organic solvent to provide the compound of formula (D):

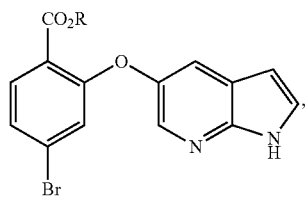
(D)

wherein R is tert-butyl;
(z) combining the compound of formula (D), wherein R is tert-butyl;
with a compound of formula (I):

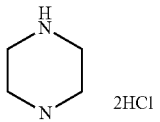
(I)

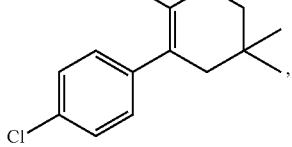

a source of palladium, a tert-butoxide salt, and a phosphine ligand in an aprotic organic solvent to provide the compound of claim 8.

* * * * *